(12) United States Patent
Abboudi et al.

(10) Patent No.: US 6,344,062 B1
(45) Date of Patent: Feb. 5, 2002

(54) BIOMIMETIC CONTROLLER FOR A MULTI-FINGER PROSTHESIS

(75) Inventors: Rochel Lieber Abboudi; Carey A. Glass, both of Highland Park; Nicki Ann Newby; William Craelius, both of Somerset, all of NJ (US)

(73) Assignees: The State University Rutgers, Piscataway, NJ (US); Nian-Crae, Inc., Somerset, NJ (US)

( * ) Notice: Subject to any disclaimer, the term of this patent is extended or adjusted under 35 U.S.C. 154(b) by 0 days.

(21) Appl. No.: 09/271,673

(22) Filed: Mar. 18, 1999

(51) Int. Cl.$^7$ .................................................. A61F 2/48
(52) U.S. Cl. ................................................... 673/24
(58) Field of Search .............................. 623/24, 25, 64, 623/62

(56) References Cited

U.S. PATENT DOCUMENTS

| | | | | |
|---|---|---|---|---|
| 3,820,168 A | * | 6/1974 | Horvath ........................ 623/24 |
| 4,175,263 A | | 11/1979 | Triplett et al. ................ 340/573 |
| 4,246,661 A | * | 1/1981 | Pinson ........................... 623/25 |
| 4,559,953 A | * | 12/1985 | Wright et al. ................. 128/680 |
| 4,575,297 A | * | 3/1986 | Richter .......................... 623/24 |
| 4,808,187 A | * | 2/1989 | Patterson et al. .............. 623/25 |
| 4,840,634 A | * | 6/1989 | Muller et al. .................. 623/24 |
| 5,336,269 A | * | 8/1994 | Smits ............................. 623/25 |
| 5,413,611 A | * | 5/1995 | Haslam, II et al. ........... 623/25 |
| 5,447,403 A | * | 9/1995 | Engler, Jr. ..................... 623/62 |
| 5,513,631 A | | 5/1996 | McWilliams ............ 128/204.23 |
| 5,662,693 A | * | 9/1997 | Johnson et al. ................ 607/49 |
| 5,888,213 A | * | 3/1999 | Sears et al. .................... 623/24 |

* cited by examiner

*Primary Examiner*—Bruce Snow
(74) *Attorney, Agent, or Firm*—Duane Morris LLP

(57) ABSTRACT

There is disclosed a control system for use with a prosthetic device comprising a sensor for sensing volitional movement of a muscle, tendon or ligament intended to cause an associated desired movement of another body part and generating an at least one signal in response thereto, and an electronic interface for analyzing at least one signal and sending a corresponding at least one control signal to the prosthetic or orthotic device indicative of the desired movement of another body part.

36 Claims, 13 Drawing Sheets

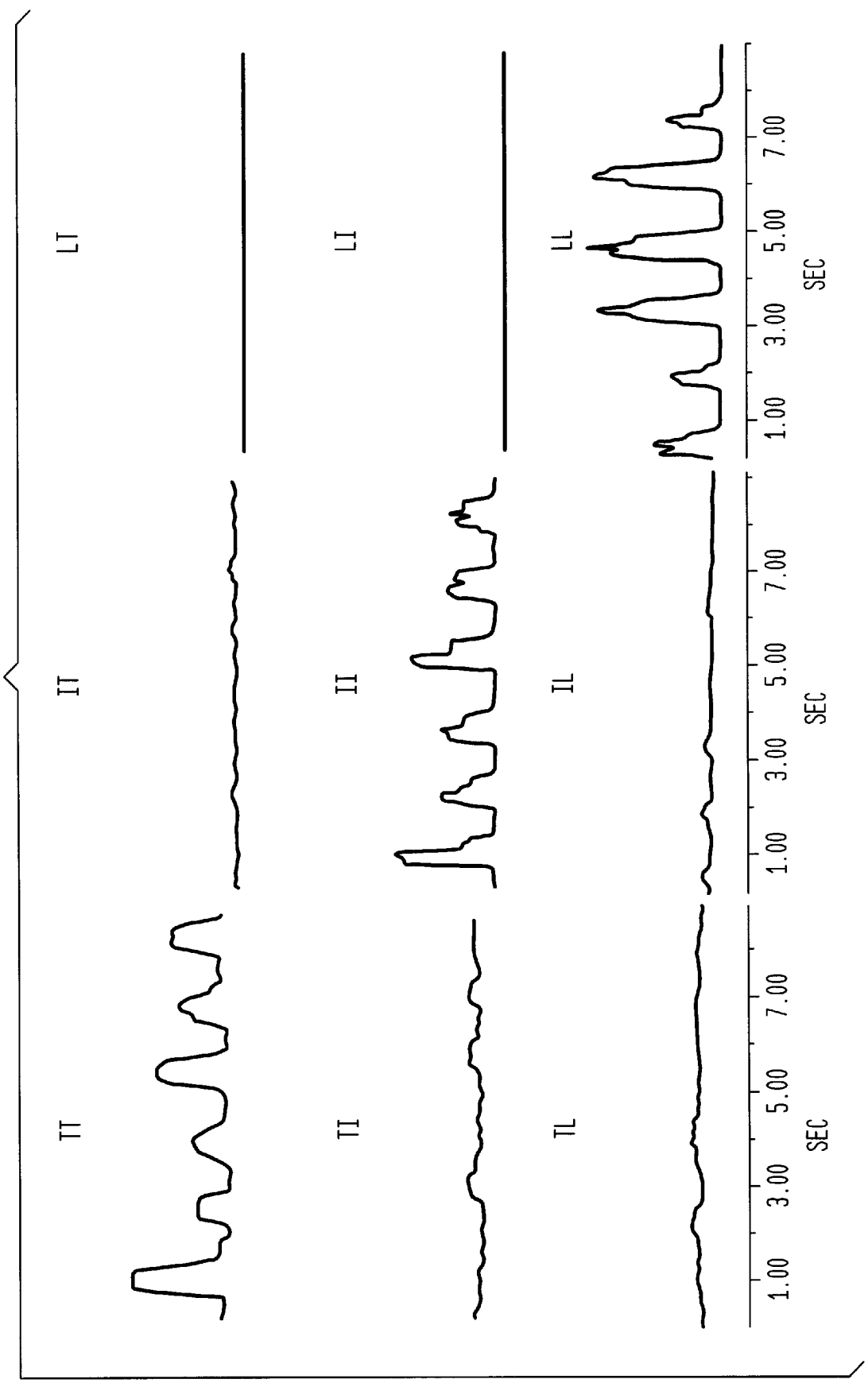

TABLE 1. RESPONSE MATRIX

| SITE → | 20T | 20I | 20L |
|---|---|---|---|
| INTENTION ↓ | | | |
| 20T | TT | TI | TL |
| 20I | IT | II | IL |
| 20L | LT | LI | LL |

TABLE 2. SIGNAL ENERGY LEVELS

| | TRIAL 1 | TRIAL 2 | TRIAL 3 |
|---|---|---|---|
| $R_{11}$ | 0.7 | -4.3 | 5.4 |
| $R_{12}$ | -0.9 | 2.6 | 6.0 |
| $R_{21}$ | 3.8 | 18.7 | 10.2 |
| $R_{22}$ | -2.0 | 22.0 | 8.6 |
| $R_{31}$ | 9.9 | 18.6 | 22.6 |
| $R_{32}$ | 9.5 | 16.9 | 22.1 |

BIOMIMETIC CONTROLLER FOR A MULTI-FINGER PROSTHESIS

This invention was made, in part, with government support under Grant R4 HD36535 awarded by the National Institute of Child Health and Human Development, U.S. Department of Health and Human Services to Nian-Crae, Inc.

FIELD OF THE INVENTION

The present invention is a control system and associated method for use with artificial limb substitutes. In particular, the present invention is a biomimetic controller for transducing volitional muscle, tendon, and ligament motions into signals that control either real or virtual movements of external limbs. It is intended for persons who either lack functional limbs, such as hands, or for those who wish to control manual devices without using their hands.

BACKGROUND OF THE INVENTION

In contrast to the dexterous manipulations performed by computer-controlled robotic hands with many-degrees of freedom, human-operated prosthetic hands function much as they did over a century ago, by single-jointed grasping. This dichotomy underscores the urgent and as yet unmet challenge of developing a versatile interface between human and machine. Specifically, the interface must accurately receive and transmit human volitional commands independently to each finger.

Present interfaces for prosthetic hands, whose function is primarily prehension, are either body powered, or myoelectric, or a combination thereof Standard body powered prostheses are controlled by a harness attached to the shoulders, that transduces shoulder flexion-extension and abduction/adduction into opening-closing of the hand. While harness-type controllers have proven reliable and robust for thousands of amputees over decades, their versatility is limited by the number of independent control motions practically possible: one. Myoelectric controllers may eventually offer more degrees of freedom (DOF), but this number is limited by the ability of the user to learn the use of non-natural movements to activate hand motions and the ability of the controller to decode the resulting electromyographic (EMG) signals. Due at least in part to these limitations, myoelectric controllers still provide only one practical DOF, directed by flexion-extension of arm muscles.

A potentially high degree of versatility has been experimentally introduced into body-powered controllers that directly attach prosthetic finger actuators to muscles whose tendons have been surgically exteriorized. However, the immediate utility of these controllers is limited by problems of tissue integration, pathological risk, and cost.

An ideal interface would sense, decode and transmit volitional signals from the original motoneuron pathways to actuators on the prosthesis. Direct hook-up to nerves transmitting biological signals thus may be the ultimate method for controlling the bionic hand, but the problems of long-term recording, as well as decoding complex spike trains, have proven formidable.

The closest alternative to biological control by nerves is biomimetic control based on the hand and finger actuators that remain intact in the residual limb. These include the extrinsic muscles and tendons controlling flexion of the metacarpal-phalangeal joints. While myoelectric recording from the individual finger-associated muscles, i.e. separate branches of the flexor digitorum, would be cumbersome, sensing their associated tendon motions appears to be more direct, since tendons directly move the fingers. Accordingly, a control system based on sensors of superficial tendon movements is desirable. The sensor should be well matched to tissue compliance and have a dynamic response range spanning the tendon force output.

A sensor system having these characteristics is part of this invention and consists of tendon-activated-pneumatic (TAP) foam sensors apposed between the skin and a hard external socket enclosing the limb. TAP sensors can transduce volitional motions of intact muscles, tendons, ligaments or tendon residua into control signals for mechanical fingers to produce finger tapping, grasping, and independently graded finger forces.

The simplest voluntary movements require activation of many muscles, and finger motions are especially complex, since each finger is controlled by activities of several dispersed muscle groups. In contrast, single extrinsic tendons directly move individual fingers. This relative simplicity of tendons and/or closely associated muscles makes them attractive controllers for hand prostheses.

SUMMARY OF THE INVENTION

It is an object of the present invention to provide a control system for use with a prosthetic or orthotic device comprising sensor means for sensing and generating at least one signal in response to volitional movement of a muscle or tendon intended to cause an associated desired movement of a bodily limb; electronic interface means for analyzing at least one signal and sending a corresponding control signal to the receiving/actuator device indicative of the desired movement of the body part.

It is a further object to provide a method for controlling the movement of an upper extremity prosthesis or orthosis in response to volitional movement of associated tendons, muscles, or ligaments corresponding to the upper extremity comprising: providing a catalog of sensed motion data corresponding to a range of motion and proportional force associated with the upper extremity; disposing and aligning a plurality of sensors onto an arm member at locations corresponding to active superficial tendons associated with extrinsic finger muscles, wherein each sensor operates to sense volitional movement of an associated tendon or muscle for causing movement of the corresponding finger and generating a deformation that causes a signal in response thereto; coupling the plurality of sensors to an electronic interface means for analyzing the signals and comparing with the catalog of motion data to generate a corresponding pattern of control signals for output to the associated upper extremity prosthesis or orthosis indicative of a desired movement.

It is a further object to provide a method for controlling the movement of a simulated hand and fingers in response to volitional movement of associated tendons, muscles, or ligaments corresponding to the hand and fingers comprising all aspects mentioned above.

It is a further object to provide a method for interfacing with a computer without a keyboard, using all aspects mentioned above.

It is a further object to provide a method for interfacing with keyboards, electronic musical instruments, games, and toys using all aspects mentioned above.

BRIEF DESCRIPTION OF THE DRAWINGS

FIG. 8 shows a signal response matrix obtained from an amputee over a 9 second period during a trial period in accordance with the present invention.

Table 1 represents an exemplary response matrix corresponding to the location of a TAP sensor and the corresponding sensing of volitional movement.

Table 2 provides exemplary signal energy levels associated with a plurality of trial runs for detecting and optimizing detected signal amplitudes associated with volitional movement of a corresponding finger.

DETAILED DESCRIPTION OF THE INVENTION

Figure 1:
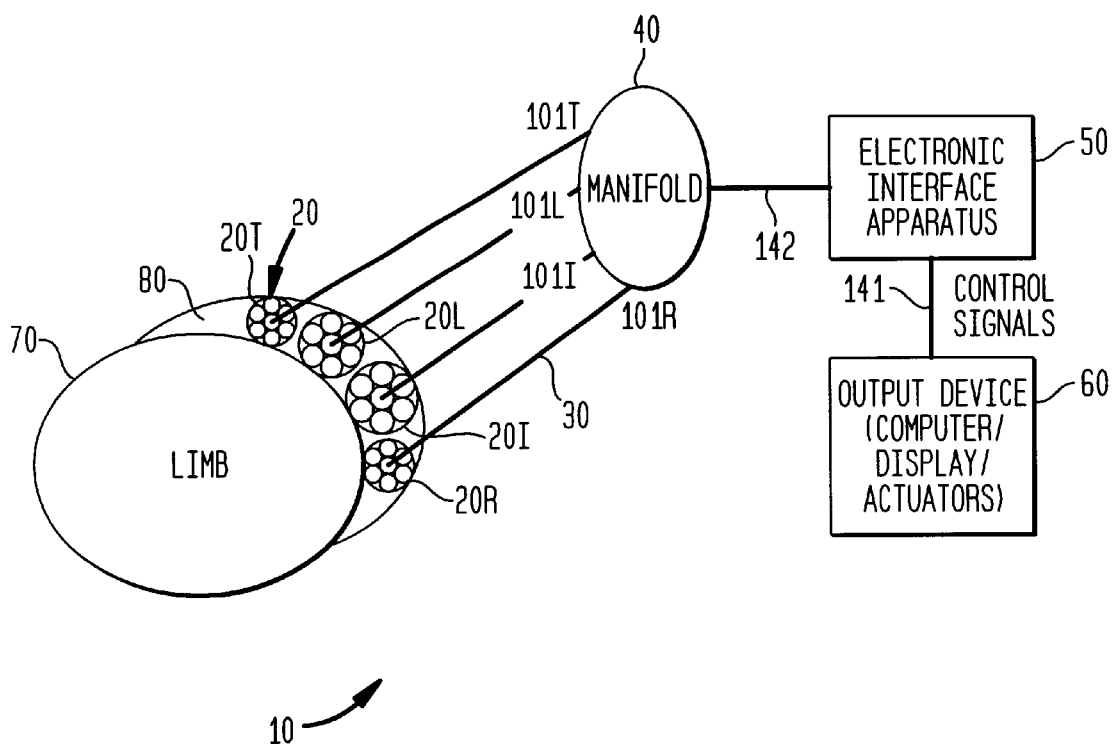
FIG. 1 is a schematic representation of the biomimetic control system according to an embodiment of the present invention.

Referring to FIG. 1, there is shown a control system for use with a prosthetic or orthotic device according to the present invention comprising a plurality of tendon activated, pneumatic sensor pads 20 positioned circumferentially on the surface of residual forearm member 70 at predetermined locations for sensing the deformation or movement of muscles, tendons, or ligaments in the residual forearm which control the movement of a corresponding respective finger on a hand. A limb socket or adjustable sensor band 80 may be placed around the forearm to secure the TAP sensors 20 to the skin. In a preferred embodiment, each limb socket contains 3–5 TAP sensor pads. The TAP sensor pads comprise small pieces of foam (open cell) sandwiched in an airtight bag or container and having a corresponding hollow tube member 30 coupled to the bag for conveying a pressure signal. The foam cell may comprise, but is not limited to polyurethane or polystyrene material. The limb sockets 80 may be fabricated in a variety of configurations, including an elastic ring wherein the sensor pads are embedded in fixed locations, a plastic band having an adhesive such as a Velcro loop aligning the interior (skin) surface, or a custom socket molded to the contours of the forearm. In this manner, the foam cell sensor pads may be embedded by lamination in a flexible sleeve molded to the limb. Such a sleeve may be made of silicone, for example.

In a preferred embodiment, the sensor pads 20 have a corresponding adhesive or Velcro hook affixed to each pad at selected locations on a plastic ring. In this manner, the plastic band closes around the arm member and locks with a buttonhole or other closure mechanism. Each of the TAP sensors operate to sense movement of an associated muscle or tendon, and to produce a pressure signal indicative of the proportional force, frequency, and degree of movement sensed and intended to cause a corresponding motion or activation of a finger. Deformations 101 T,I,L and R from each of the TAP sensors 20 are conveyed via a pressure differential in the corresponding tubes 30 which are coupled to a manifold 40. The manifold 40 has a plurality of cavities, where each cavity is operable for receiving a corresponding tube 30. Each tube 30 may be inserted into each of the corresponding cavities or holes. The manifold operates to collect the tubes into a single multi-lumen tube 142 for input into an electronic interface signal processing and detection apparatus 50. Alternatively, each tube 30 may insert directly into a corresponding cavity on the electronic interface apparatus 50. The electronic interface 50 includes pressure transducers, amplifiers, a microcontroller, RAM memory and output means for sensing, transducing, processing and detecting the received signals from the TAP sensors and generating a pattern of output control signals to an output device such as a prosthetic hand or a computer.

In a preferred embodiment, the electronic interface apparatus 50 utilizes a combination of hardware and software functionality to perform its associated processing functions. The apparatus includes two computer programs: a training program that will generate a library of movement patterns within memory, and an operational program that decodes incoming signals representing requested finger motions and sends control signals 141 to an output device 60 including either another computer or to finger actuators on a mechanical hand or to other output devices. The training program can record movements made by intact hands, and display them dynamically to the user, who then will attempt to mimic those movements with volitional signals from the sensors attached to the limb socket. The training program will then record each signal pattern, keyed to specific movements, in a computer library such as a data base or flat file. The operational program has signal processing capability with pattern recognition software for detecting and determining finger movements, based on the library catalog. These movements will include repetitive tapping, grasping, and graded finger force applications.

Figure 3:
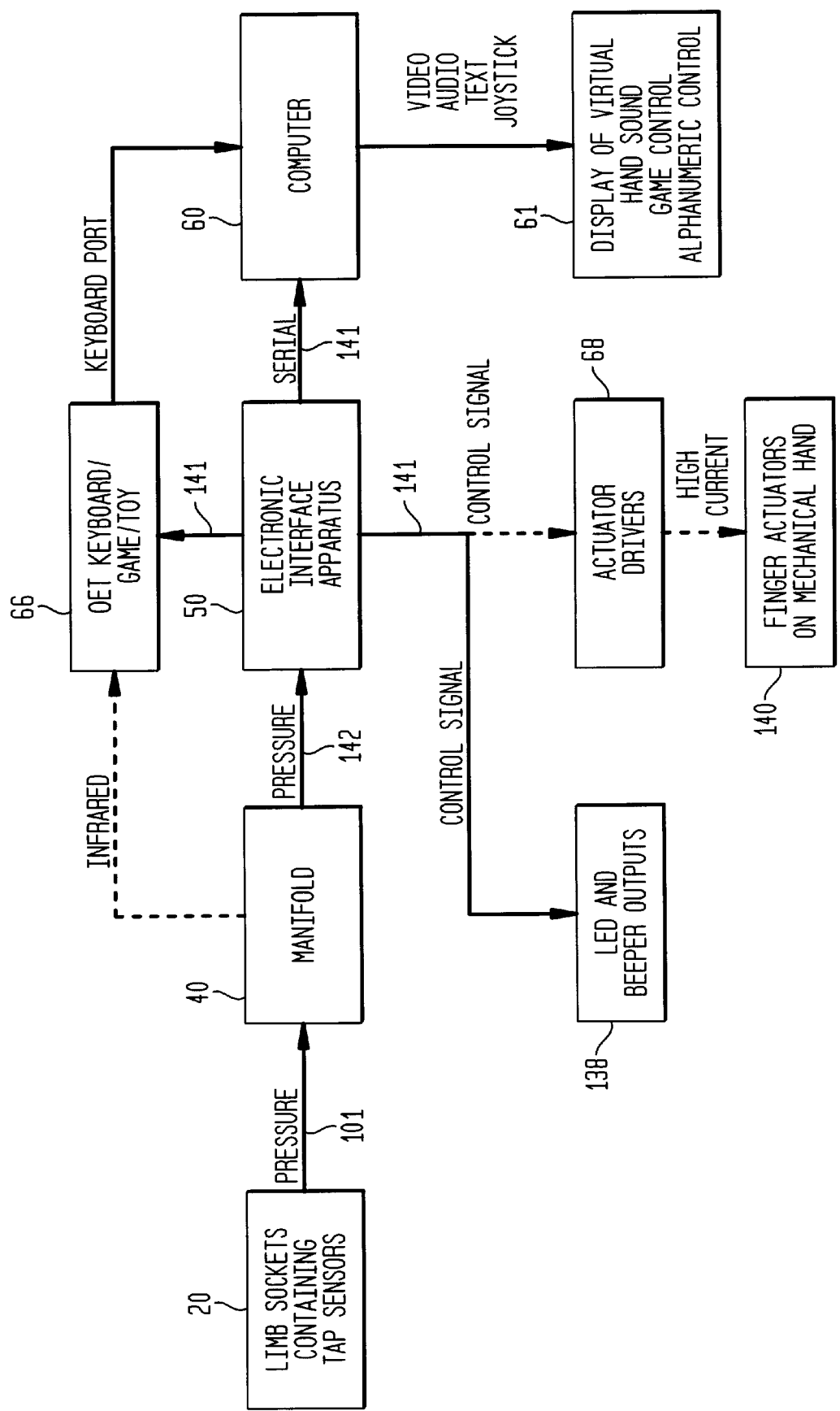
FIG. 3 is a block diagram showing each of the major components associated with the tendon-activated pneumatic controller according to an aspect of the present invention.

In the preferred embodiment, the controller 10 according to the present invention is designed to interface tendons in the residual forearm with multiple fingers of a mechanical or virtual hand 140, with both grasping and tapping capabilities via control signals for driving actuators 68 (see FIG. 3). Alternatively, the controller may also drive other output devices such as a computer having a graphical display for displaying associated finger movement or providing user feedback regarding intended movement via audio, video or manual responses or for which the controller may provide input which substitutes for a keyboard, mouse, or game controller; or electronic keyboards operable to associate particular control signals with associated keys for typing or sound generation; or electronically controlled games and toys.

Figure 2:
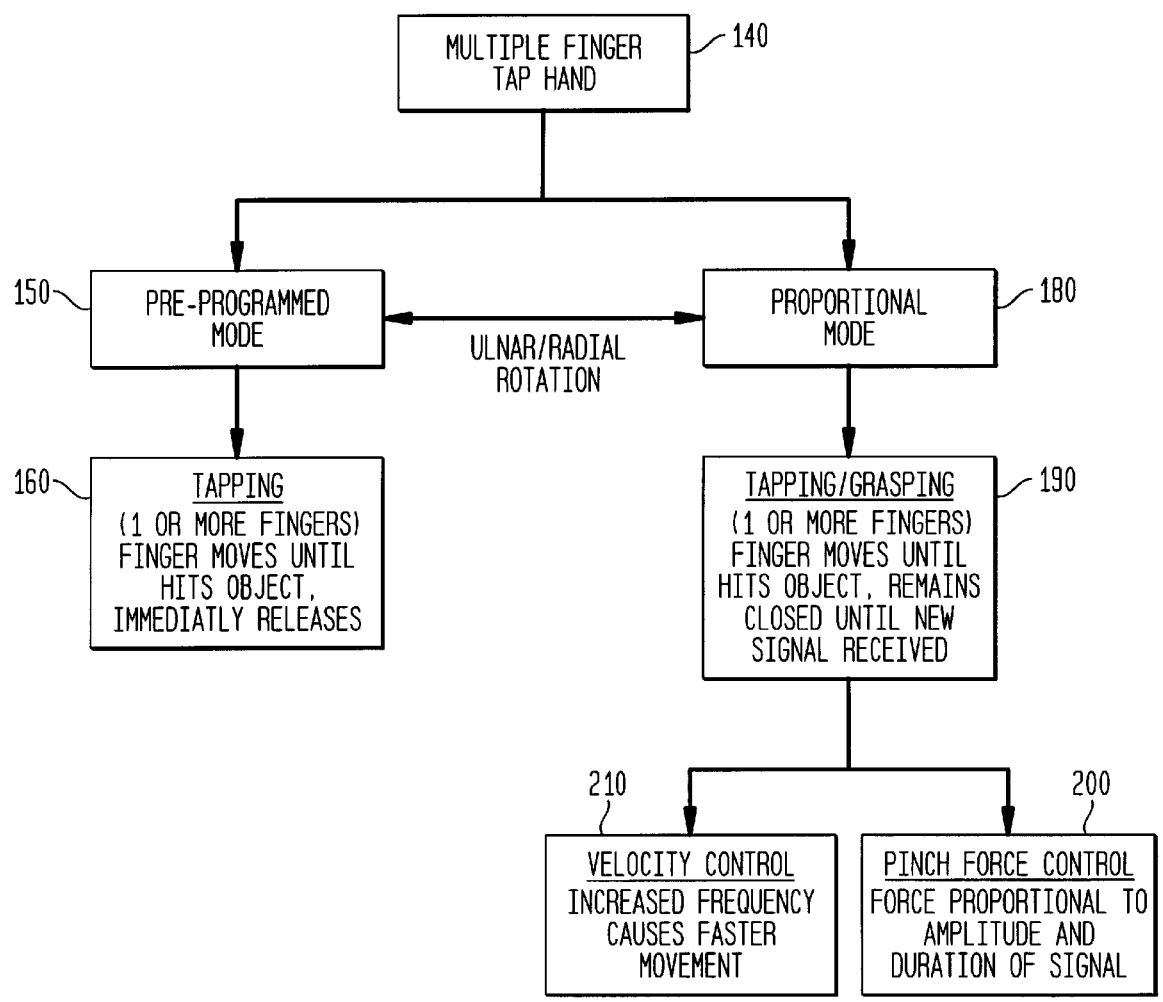
FIG. 2 shows a flow diagram of the dual-mode controller having pre-programmed and proportional modes of operation according to an aspect of the present invention.

In a preferred embodiment, two main operational modes are included, as illustrated in FIG. 2: a pre-programmed mode 150 and a proportional force mode 180. Mode switching is accomplished via patterned rotations of the forearm that activate the ulnar/radial TAP sensor 20R which operates to generate a signal 101R (FIG. 1) to the electronic interface apparatus for switching the mode of operation. In either mode, the controller functions to flex the desired finger or fingers in response to an activated TAP sensor until they contact an object, as sensed by sensors (not shown) in the mechanical hand or output device.

Referring now to FIG. 2, in conjunction with FIGS. 1 and 3, in pre-programmed mode 150, volitional movement of muscles, ligaments and tendons associated with a particular finger causes a corresponding TAP sensor to be deformed, thus generating a pressure signal 101/142 which is detected and processed by electronic apparatus 50, which generates a corresponding control signal 141 to move that finger or to control a specific function of a device such as a keyboard, game or toy. Each finger will then release (extend) upon contact 160. The pre-programmed mode is relevant to tasks such as typing and keyboard tapping. Thus, in this mode, thumb motion would be circumduction, instead of flexion.

In proportional force mode 180, the fingers and/or thumb remain flexed on an object until extended by a volitional release signal as indicated in block 190. The applied force 200, as well as velocity (i.e. frequency) 210 is controlled voluntarily by the degree of motion and deformation sensed by the TAP sensors. In a preferred embodiment, the proportional force mode may operate as the default mode for most users, while the pre-programmed mode is intended for use in tasks such as typing or piano playing.

Figure 4:
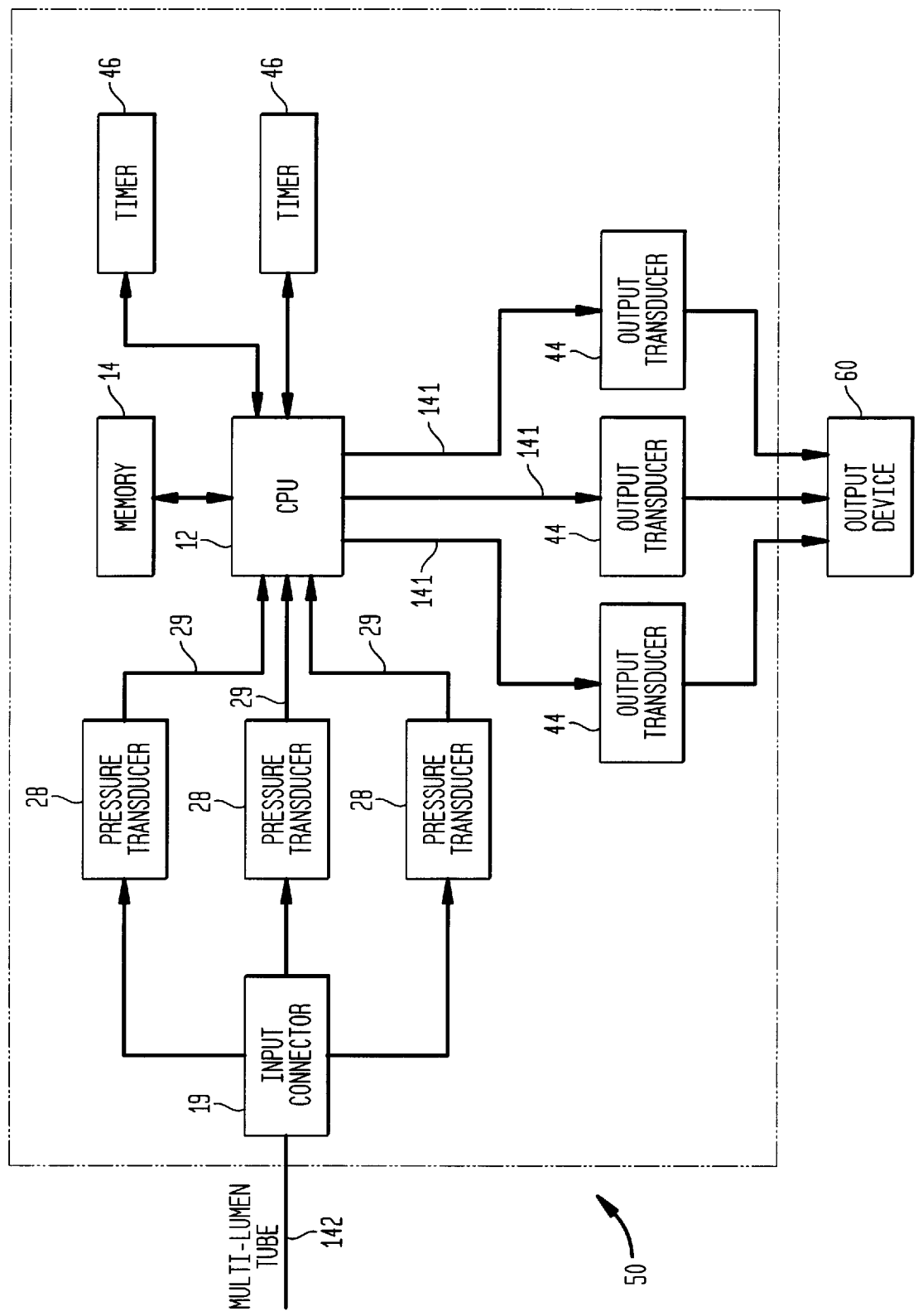
FIG. 4 is a schematic diagram of the electronic interface apparatus for processing and detecting signals associated with intended finger movement according to an aspect of the present invention.

In a preferred embodiment, the electronic interface apparatus 50 is of a similar type to that described in U.S. Pat. No. 5, 333,615 issued Aug. 2, 1994 to Craelius & Newby, the inventors herein, the description of which is hereby incorporated by reference, modified by the addition of input pressure transducers 28 (see FIG. 4). A schematic of the electronic interface apparatus is illustrated in FIG. 4. As shown in FIG. 4, the interface apparatus 50 operates to digitally record and analyze the pressure signals from activated TAP sensors and includes a microprocessor or central processing unit (CPU) 12 for controlling the various operations, memory means 14 for storing software programs including routines which allow the CPU to perform various types of data collection and to output control signals to various output devices, a plurality of pressure transducer means 28 for transducing pressure into digital data, a plurality of timer devices 46 for timing of input and output data, and a plurality of output transducers 44 for generating signals from the CPU to an output device 60. Memory 14 further includes data corresponding to TAP sensor activation threshold criteria for comparing with received TAP sensor signals for enabling finger movement detection and proportional force application.

As shown in FIG. 4, the electronic interface apparatus 50 comprises input connector 19 for receiving from multi-lumen tube 142 or a plurality of single lumen tube signals 101 from manifold 40 (see FIG. 1, FIG. 3 ). Connector 19 comprises a plurality of input channels, each corresponding to a particular one of the tubes 30 associated with a corresponding TAP sensor. Input pressure transducers 28 are connected to each of the corresponding input channels for transducing the received pressure signal into a corresponding electrical signal 29 for signal processing and detection and include A/D converters for digitizing the received analog input. The signal from each sensor channel is then processed to produce a signal replica of each signal. Each signal replica from all sensors is then combined into a composite signal that is used to represent the ongoing commands of the user. The composite signal is continually processed in conjunction with information stored in RAM 14 to determine what motions are being requested by the user. Upon decoding the composite sensory signal, a corresponding pattern of control signals 141 will be sent by the CPU 12 to output transducers 44 connected to actuators or other devices 60. Timers 46 are coupled to CPU 12 and act in conjunction with the detection and analysis of input signals 29 and the synthesizing of control signals 141 to determine the trajectory and speed of finger motions. In this way the commanded sequence of movements will be executed by the control system.

Simple motions may be decoded with simple analysis algorithms. For example, simultaneous detection of finger movement from at least three separate TAP sensors (actually detection of at least three fingers occurring within a pre-defined timer window set by timer 46) may be indicative of a grasping motion, whereas detection of motion of a plurality of fingers occurring at time intervals outside a predetermined time window set by timer 46 may be determined by CPU 12 as indicative of a tapping motion.

The electronic interface apparatus 50 may operate to send control signals to an output device comprising a host computer or display 60, an opto-electronic tactile keyboard or an electronically controlled game or toy 66, or an actuator driver 68 for driving the finger actuators on a mechanical hand 140, depending on the mode or configuration of the controller, as illustrated in FIG. 3.

Figure 7:
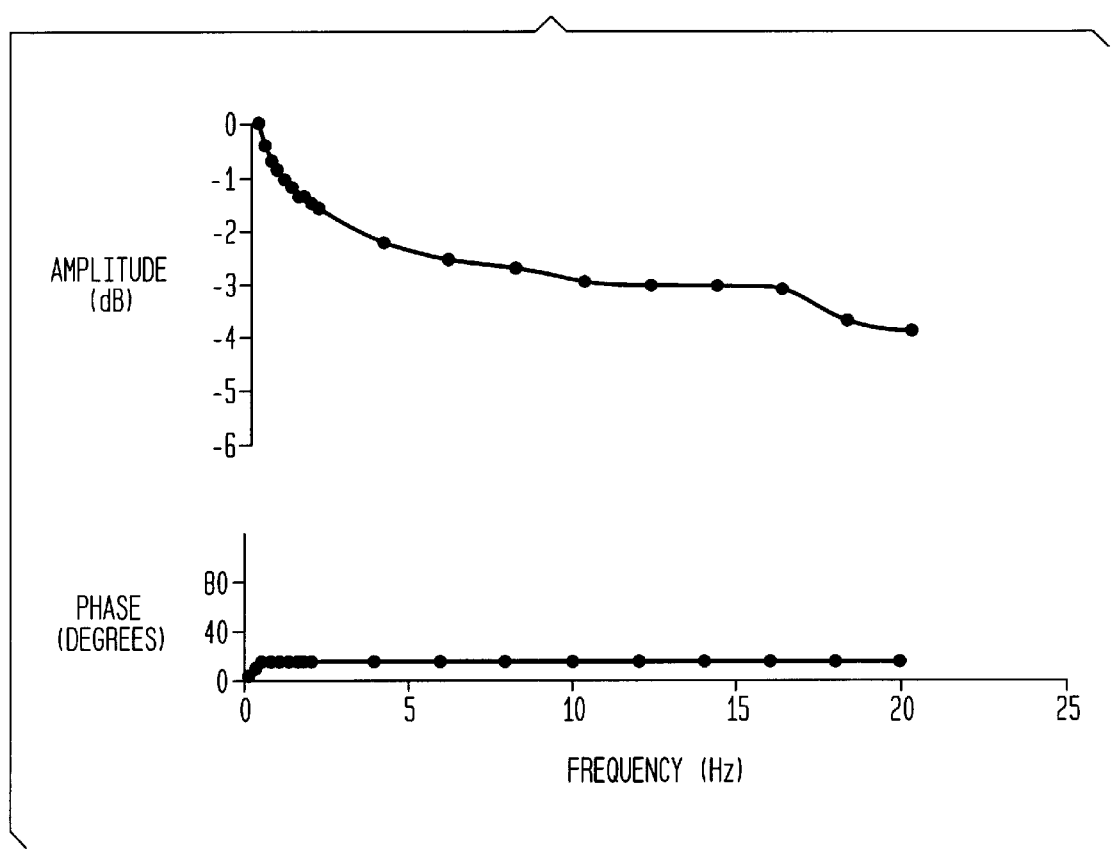
FIG. 7 is a Bode plot of a typical TAP sensor.

Referring again to FIG. 1, the tendon-activated pneumatic (TAP) sensors are preferably fabricated from porous open-cell foam, sealed within a polyethylene or polyvinyl bag and attached to a flexible tube. The tubing 30 forms a connection between the TAP sensors and pressure transducer. The TAP sensors operate to detect displacements of the tendons, muscles, or ligaments. Foams are selected to provide a range of response time constants and compliance to match with specific tissue properties. Note that transducer characteristics of the TAP sensors, such as calibration and frequency response, are dependent on foam type and density. Typical frequency response characteristics for a typical TAP sensor are shown in FIG. 7 . In this embodiment, signals from TAP sensors were amplified to a range of −2.5 to 2.5 Volts and were digitized at 200 Hz each with 16-bit accuracy, and displayed on a Pentium computer.

Figure 5:
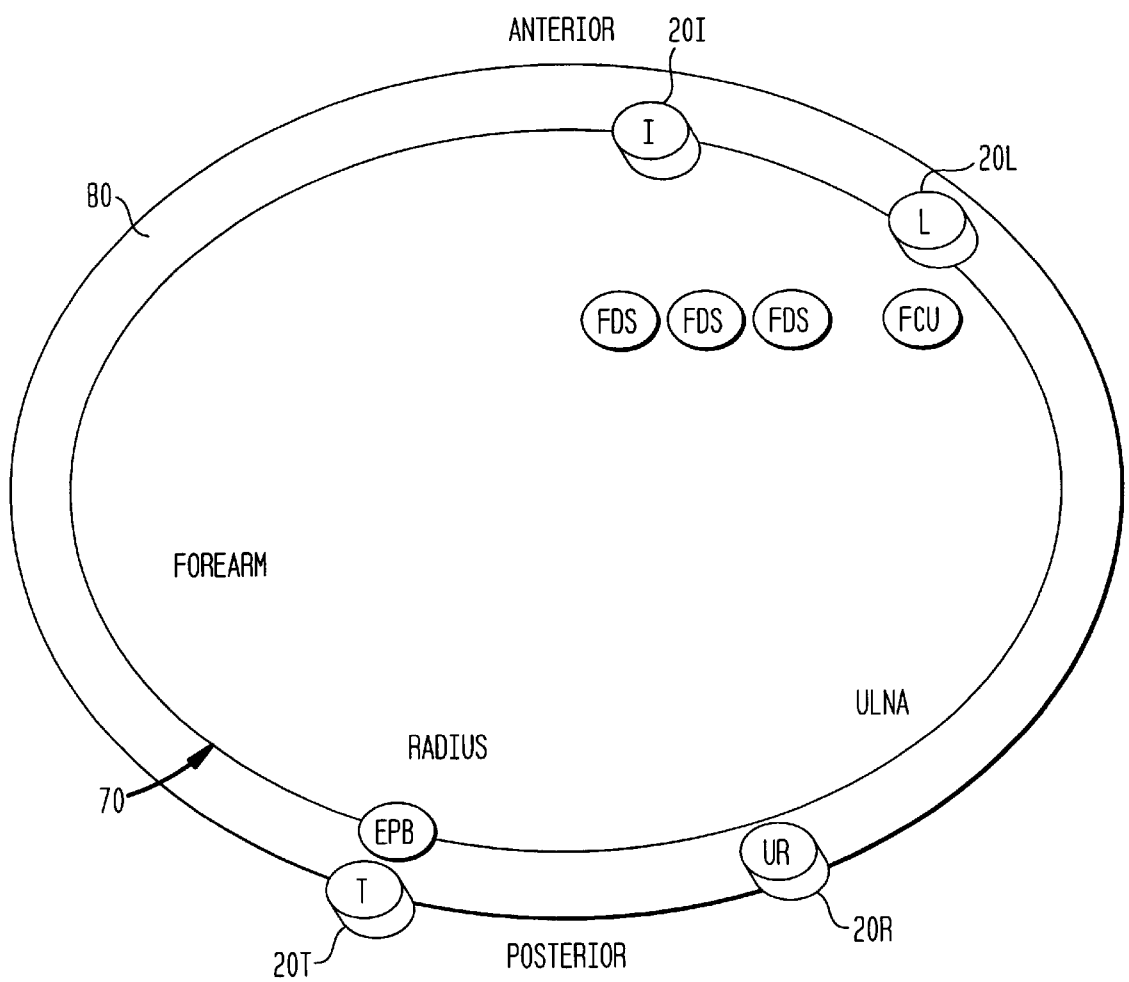
FIG. 5 is a cross-section of an exemplary anatomical sensor placement based on desired motion according to an embodiment of the present invention.

The TAP sensors may also be placed directly into a prosthetic socket, as shown in FIG. 5. Note that one of the problems associated with the prior art (myoelectrodes) is the concern among amputees of a short circuit upon contact with sweat. Due to the tight fit of sockets, this drawback is serious and applies to almost any exertion. The present invention eliminates this problem as pneumatic foam sensors are impervious to sweat, and thus much preferred over metal electrodes.

Figure 6:
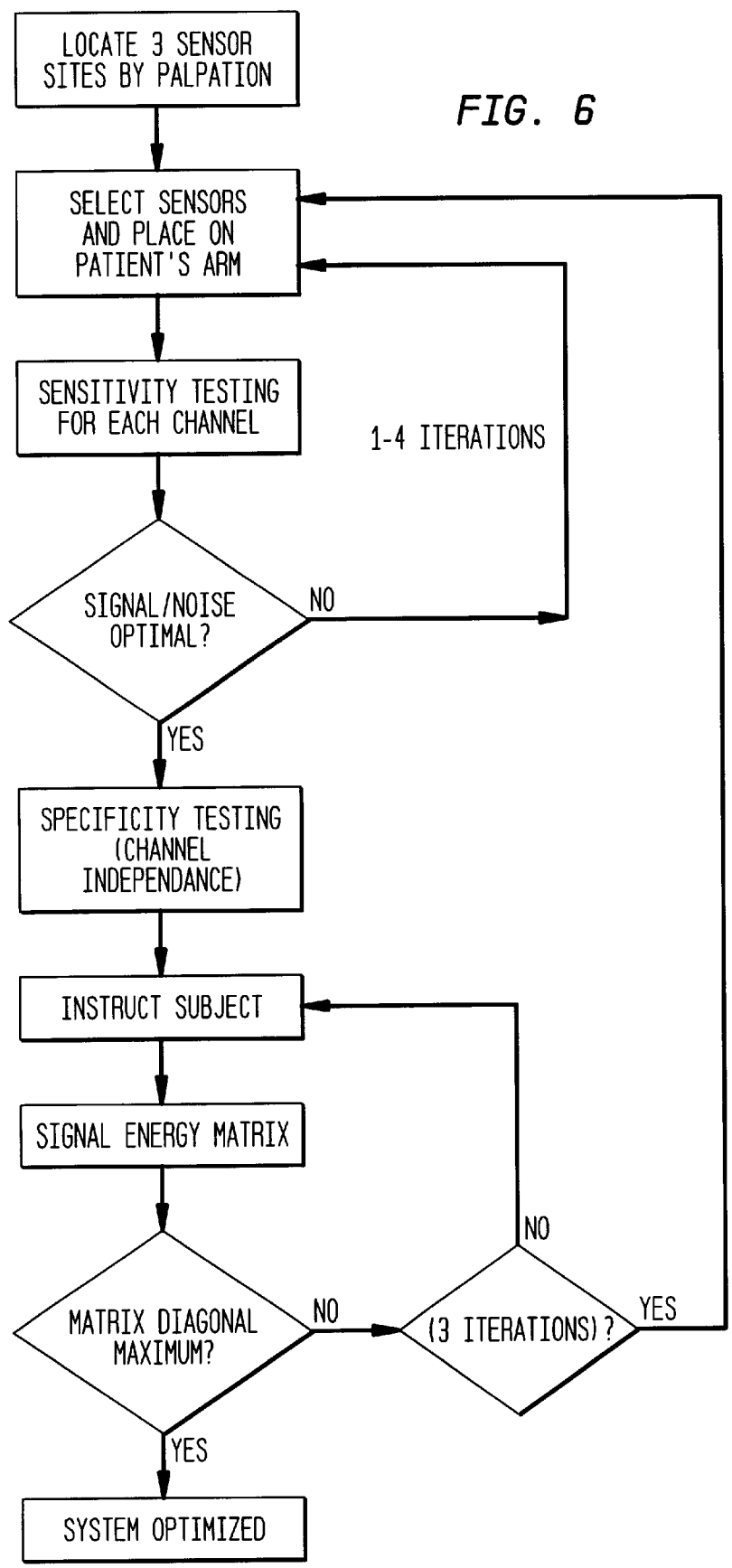
FIG. 6 is a flow chart depicting the steps involved in system controller optimization.

Referring now to FIGS. 5 and 6, there is illustrated the location and method for placement and optimization testing of the controller according to an embodiment of the present invention. Candidate TAP sensor locations are circumscribed by palpating the forearm 70 during volitional finger motions. These preliminary sites correspond to sites of specific tendon, muscle, or ligament movements as illustrated in the forearm cross section shown in FIG. 5. The extensor pollicis brevis tendon (EPB) corresponded to the placement site of the thumb sensor (20T). The flexor digitorum superficialis tendons (FDS) corresponded to the site for the index finger sensor (20I). Motion of the little finger (20L) was associated with movement in the flexor carpi ulnaris tendon (FCU). An additional sensor 20R was positioned between the ulna and radius to detect forearm rotation for hand motion and/or mode switching.

After initial demarcation of sites of specific movements on the external surface of arm 70, the next step is to position several TAP sensors, i.e., 20I, 20L, 20R, and 20T near them.

Note that while only four sensors have been shown, additional sensors may be disposed on the arm member corresponding to each finger as well as to wrist or hand rotation. Placement of sensors may be done by a therapist or by the user themselves. Then either a prosthetic socket or an adjustable plastic cuff 80 is placed over forearm 70, tightly apposing the TAP sensors against the skin. A flowchart depicting the sequence of steps for optimizing the control system for detection is shown in FIG. 6. To initially locate the site of maximum response, a trial sensitivity session is preferably conducted, wherein the responses of a particular user to sequential movement prompts are recorded, while the sensors are moved within a candidate region on the forearm. Preferably, a maximum of four iterations for each set of sensors is performed to determine the best locations, having the highest sensitivity, based on highest signal to noise ratio (SNR).

After maximizing the response from each TAP sensor, the next step is to optimize specificity by training the user to evoke the correct signals with minimum effort. First, the user is prompted by a programmed computer display to produce a sequence of simple movements of finger(s). These movements are transduced and corresponding signals are input to the computer. Each requested movement generates a response matrix, comprising three rows, representing the requested finger motion, and three columns, representing the three sensor locations for a particular movement, as illustrated in Table 1. Thus, each movement will produce signals from all three channels, as displayed across the row representing that requested movement. TT, for example, represents signals received from the thumb sensor 20T for an intended thumb movement, while LT represents a signal sensed from the same sensor 20T for an intended little finger movement, and so on. Optimal response is obtained by maximizing the diagonal relative to the off-diagonals of the response matrices. If the relative amplitudes of diagonal signals are inadequate, the user is instructed to modify his force to help avoid cross signals. If, after 3 iterations, the desired results are still not achieved, sensor placement is changed, and the process of determining sensitivity and specificity begins again. After the TAP sensor system placement is optimized and fixed in place with the cuff or socket, the user will train the controller to duplicate motions of his volition. The user will have alternative means of training the controller, depending on his function. For users possessing at least one sound hand, there may be a sensing glove available for them to input desired motions into the computer. The user will then command those same motions from his other hand (i.e. missing or dysfunctional hand), while the composite TAP signals from his arm are recorded. The computer will then place the sequence of composite signals corresponding to specific movements in a library of memory. The library will then be adapted for insertion in the hand controller for use. Specific movements of the hand will be executed when the incoming signal composite matches, to a statistical likelihood, a specific pattern in the library.

Alternatively, a pre-programmed library of finger animations will be displayed to the user, who will attempt to mimic selected movements.

A typical training session may ensue as follows: The user with one sound hand first uses the glove to enter a sequence of individual finger taps, grasping and releasing of a cup, and a sequence of finger movements of increasing force. The computer stores the movement sequences from the sensors in the glove, and uses a virtual reality software program to animate those movements. Then the user, either simultaneously with or subsequently to the sound hand movements, commands similar movements from his missing hand. The composite TAP signals are recorded in a library, called input library and indexed to the requested motions. Then the input library can be downloaded to the hand microcontroller, which will use the library to compare subsequent TAP input signals with the library patterns and thus generate a pattern of pulses to create each desired type of movement.

As previously mentioned, detection of sequential simple tapping or grasping motions can be accomplished by comparing the signals received from each channel against a pre-set threshold. In this embodiment, grasping is indicated when thresholds for all three fingers are exceeded simultaneously.

Figure 9A:
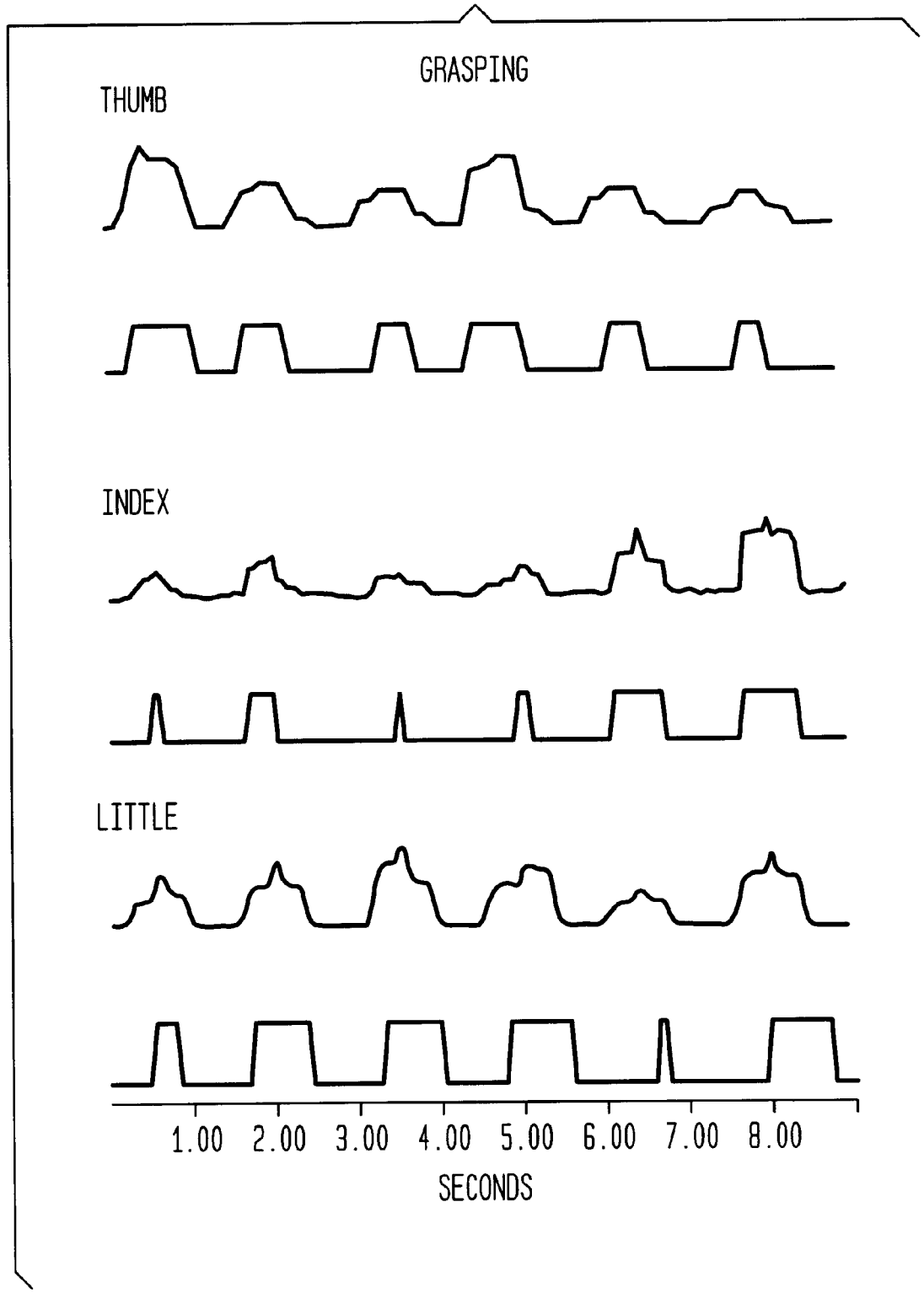
FIGS. 9A–B show grasping versus sequential tapping responses obtained using the controller of the present invention.
Figure 9B:
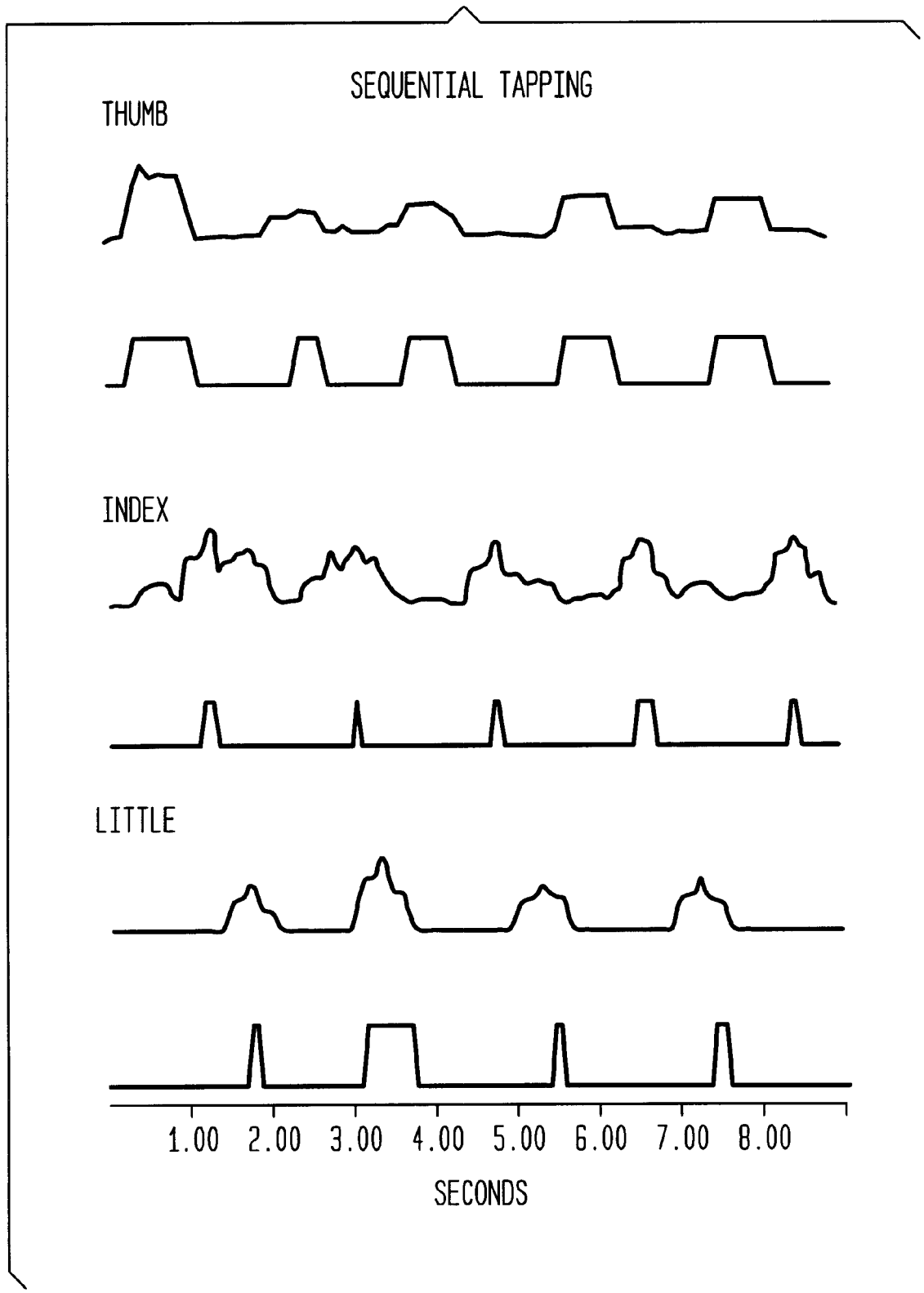

Note further that, in the preferred embodiment, signal energies (squared amplitudes) from TAP sensors range from 5–40 $(mV)^2$. A typical response matrix is shown in FIG. 8. Note that the diagonal signals are large relative to the off diagonals, ranging from 5 to 25 dB, as listed in Table 2. These results are representative of those obtained from six amputee subjects. FIG. 9A shows the results of grasping by an amputee subject. Note that, although absolute signal amplitudes from each finger varied, each exceeded their threshold during the repetitive grasps, indicating detectability of grasping volition. The simultaneity of the three finger activations indicated correct response each time. These records were elicited by the amputee on his first try after he was asked to grasp with his phantom fingers. Sequential tapping was similarly successful for the amputee as shown in FIG. 9B. Note that the tapping was detected repetitively with 100% accuracy for the thumb-index-little finger sequence.

Figure 10:
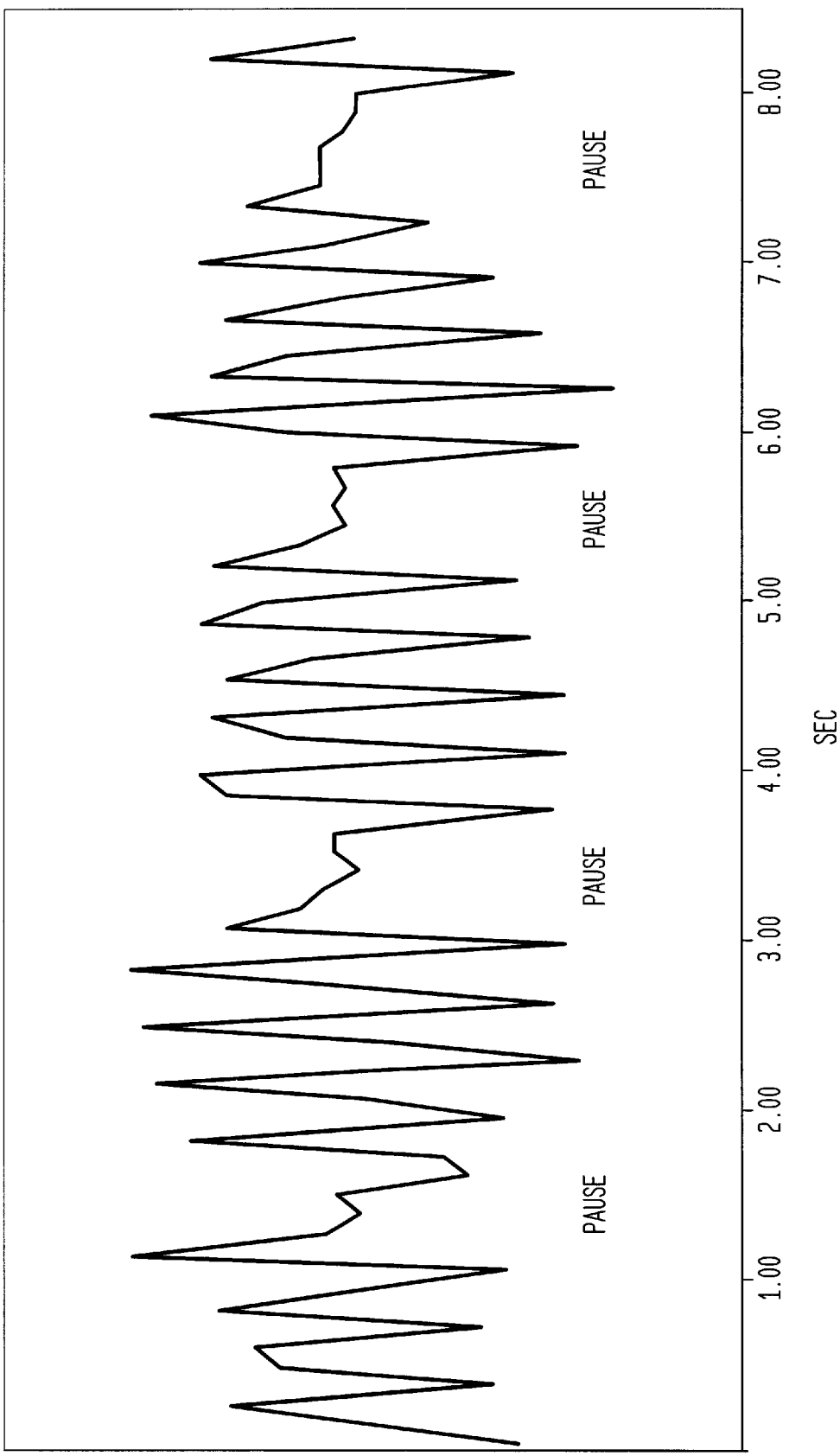
FIG. 10 shows a maximum frequency response using the controller of the present invention.

A subject was tested to assess maximum response rate of TAP sensors. As shown in FIG. 10, the sensor responded adequately to the maximum tapping frequency for the subject which was about 3 Hz.

Figure 11:
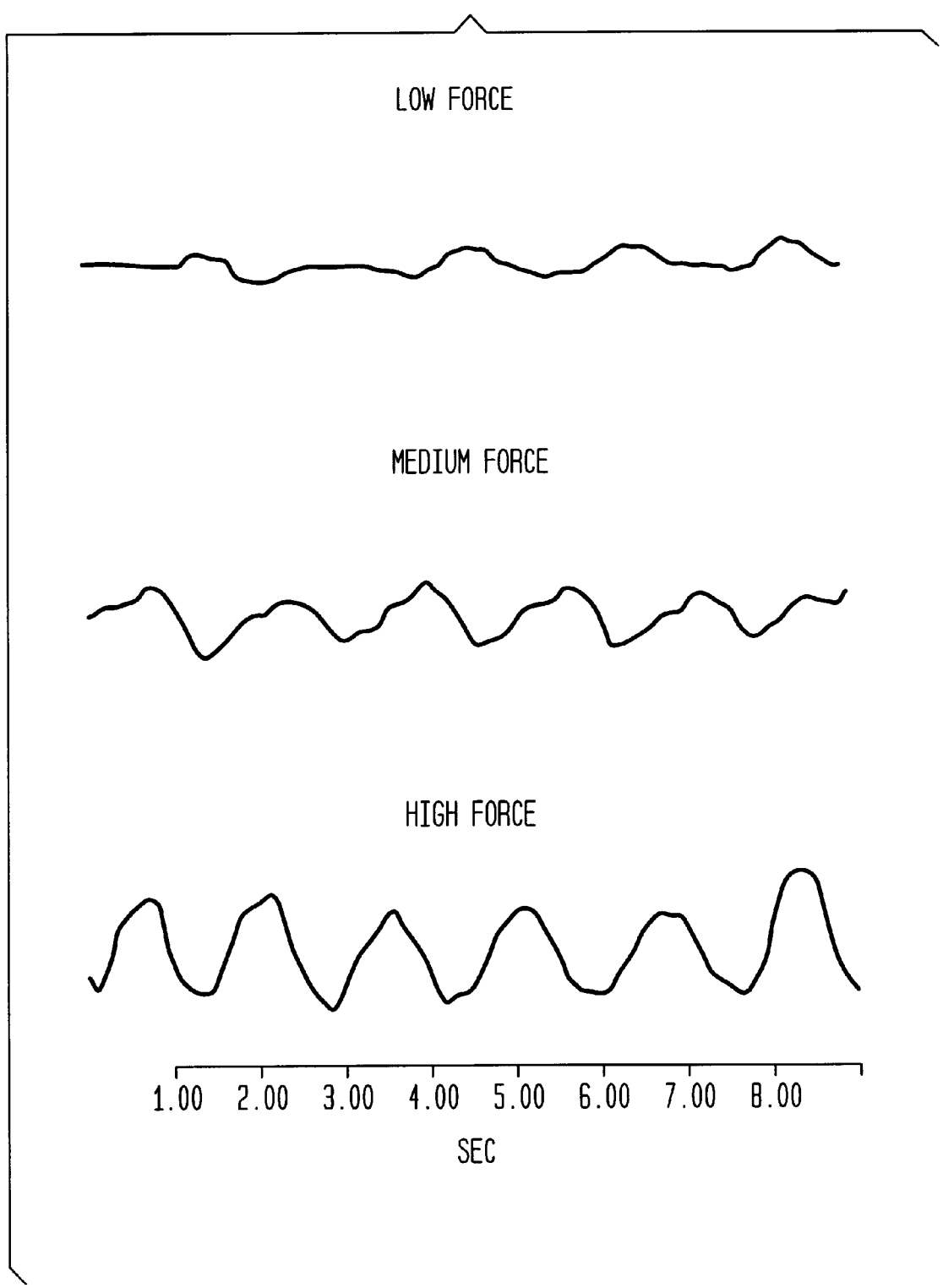
FIG. 11 shows a proportional force response using the controller of the present invention.

To demonstrate the proportional force capability of TAP sensors 20, first the ulnar/radial switch sensor 20R was activated in order to place the controller 10 in the proper mode. The protocol involved prompting one to quickly rotate the forearm twice. Signals from the ulnar/radial sensor exceeded 25 dB (not shown), indicating more than adequate signal for high reliability switching between modes. After switching to the proportional force mode, the subject was asked to apply three pinches of increasing intensity, as shown in FIG. 11. The sensor responded approximately in proportion to the subjectively determined force intensity, indicating the proportional force capability of the TAP sensors.

Note that the number of degrees of freedom of the controller 10 is limited by the number of distinctive movements on the upper extremity that can be transduced and decoded. The most accessible structures are generally the four superficial flexor tendons and associated muscles and ligaments corresponding to each finger, and the superficial thumb extensor. Note that it is possible that the extensor tendons on the posterior arm (for the four fingers), and the thumb flexor could also be sensed, providing up to ten separate control channels. However, since the tendons are flexion/extension pairs, they may practically represent only five independent DOF. While other signals from muscles may be added to the controller, this may compromise the biomimetic nature of the design.

The TAP controller offers for the first time a simple non-invasive transduction of finger tendon motions. With simple addition of two sensors, the system may operate to control a five-finger hand under direct command from natural motoneuron pathways. Thus, the TAP controller exceeds the capabilities of present controllers in several categories.

An additional advantage beyond providing finger control to hand prostheses is that the TAP controller may facilitate the transition to more complete hand restorations. It must be recognized that a necessary prerequisite to surgical reconstruction of the hand, or direct connection of nerves and prosthesis, is an intact motor control system. Disuse of the latter, which usually accompanies amputation or cases of congenital upper limb reduction deficit, causes irreversible neuronal reorganization and deterioration. Early use of a biomimetically-controlled controlled hand, especially in children, might preserve the musculature and associated nerve pathways that may eventually be needed as controllers of the future transplanted or hybrid hand.

Referring collectively now to FIGS. 1–6, the controller 10 according to the present invention, may serve both as a stand-alone system for training and testing, as well as the controller of a mechanical hand or orthosis. The operation proceeds as follows. The user places several sensors 20 on a sensor band 80 using an adhesive, such as a Velcro attachment. The bands are strapped onto a limb or forearm, and the sensors are aligned over locations corresponding to active, superficial tendons, muscles and ligaments corresponding to individual fingers. Guidelines for location of the sensors may be provided based on catalogued anatomical or physiological information. Tubes 30 emanating from the sensor band are then plugged into a manifold 40, whose output is then attached to an electronic interface apparatus 50. The electronic interface is coupled to an output device such as a computer, keyboard, mechanical hand 60 (or orthosis). The user then tries to move his fingers and, based on the output device, feedback is provided regarding his success. In the case of a computer having a screen display and sound card, the computer may be programmed to provide suggestions and feedback regarding relocating the sensors in order to optimize the TAP finger sensor signals. The information concerning the users signal amplitudes for detected finger motion may be stored in a database housed in RAM memory. Preferably, several sub-modes of operation will also be available and based on user-selectable criteria. One sub-mode may represent a virtual hand comprising a graphical display on the computer screen of a target hand and its fingers which move in response to the user commands, based on a pattern of control signals output from the electronic interface apparatus and indicative of the sliding motion of the associated tendon. The second sub-mode comprises a game hand which allows the user to play with third party games or toys using finger motions produced with TAP sensor signals, which game hand may optionally include remote control capability. The third mode of operation may be a piano or alphanumeric keyboard or opto-electronic tactile (OET) keyboard 66 (see FIG. 3). In this sub-mode, the user would position and move his forearm or limb 70 along the keyboard to select individual notes by activating a particular finger. In the case of a piano keyboard, this may be coupled to computer 60 via a keyboard port to produce appropriate sounds via a sound card housed within the computer, or may include its own microprocessor and speaker system to produce the sounds. The OET would have photodiodes attached to each key, to sense the position of the limb, that would have an LED attached. In the case of an alphanumeric keyboard, it will be possible for the user to perform typing tasks. Sub-mode 3 thus corresponds to pre-programmed operational mode 150 (see FIG. 2) of the controller managed by CPU 12. Sub-modes 1 and 2 correspond to proportional mode 180. Additional sub-modes of operation and/or output devices may be controlled by a series of control signals including TTL signals, pulse width modulated signals, or serial communication signals, and may include orthoses that aid a person with neurological deficiencies.

It will be understood that the embodiments described herein are exemplary, and that a person skilled in the art may make many variations and modifications without departing from the spirit and scope of the invention. For instance, while the preferred embodiment depicted herein discloses the use of TAP sensors for generating pressure signals, other non-pressure signals generated from other types of sensors, such as silicon strain gauge sensors, are also contemplated. All such modifications are intended to be included within the scope of the invention as defined in the appended claims.

What is claimed is:

1. A control system for use with a prosthetic or orthotic device comprising:
    at least one pneumatic sensor for sensing volitional movement of a muscle, tendon or ligament intended to cause an associated desired movement of another body part and generating at least one signal in response thereto; and
    electronic interface means for analyzing said at least one signal and sending a corresponding at least one control signal to said prosthetic or orthotic device indicative of said desired movement of said another body part.

2. The control system according to claim 1, wherein said sensor means comprises a plurality of tendon activated pneumatic (TAP) sensors.

3. The control system according to claim 2, wherein said plurality of TAP sensors comprise foam cell sensor pads and including means for pressurized air flow.

4. The control system according to claim 3, wherein said foam cell sensor pads are made of open cell foam.

5. The control system according to claim 3, wherein said foam cell sensor pads are embedded by lamination in a sleeve, for positioning on a limb.

6. The control system according to claim 1, wherein said electronic interface means comprises:
    input channel means for receiving said at least one signal;
    transducer means for transducing said at least one signal into a corresponding at least one electronic signal to be processed;
    signal processing means for performing signal analysis and signal processing of said at least one electronic signal for detecting and determining the degree of movement desired of the another body part for generating said at least one control signal;
    memory means for storing information associated with said electronic signal; and
    microprocessor means for controlling the storage of said information in memory and the sending of said at least one control signal to said prosthetic or orthotic device.

7. The control system according to claim 1, wherein said at least one signal is a pressure signal.

8. The control system according to claim 6, wherein said at least one signal is a pressure signal, and wherein said transducer means comprises a pressure transducer.

9. The control system according to claim 1, wherein said prosthetic or orthotic device comprises a mechanical device allowing manual manipulation of digits.

10. The control system according to claim 1, wherein said prosthetic or orthotic device comprises a host computer having display means for displaying information associated with said desired movement of said another body part from said at least one control signal.

11. The control system according to claim 1, wherein said prosthetic or orthotic device comprises an optical-electronic-tactile (OET) keypad.

12. The control system according to claim 1, wherein said associated tendons, muscles, or ligaments are associated with extension or flexion of fingers.

13. The control system according to claim 1, wherein said associated tendons comprise superficial tendons, each said tendon corresponding to an associated finger, and a superficial thumb extensor or flexor tendon corresponding to a thumb for providing movement thereto.

14. The control system according to claim 1, wherein said prosthetic or orthotic device comprises a game or toy.

15. The control system according to claim 1, wherein the associated muscles, tendons, or ligaments comprise flexion/extension pairs of tendons, muscles or ligaments.

16. The control system according to claim 2, wherein said another body part comprises a hand and a plurality of fingers including a thumb, and wherein each of said TAP sensors is for externally positioning on an associated muscle, tendon or ligament to sense movement of the associated tendon corresponding to a particular one of said fingers or hand for movement thereof to generate a pressure signal corresponding to a degree of volitional movement associated with said finger or hand.

17. The control system according to claim 3, further comprising a manifold coupled between each of said TAP sensors and said electronic interface means for receiving a plurality of pneumatic tubes, each said tube coupled to a corresponding one of said TAP sensors for conveying pressure signals and forming a single multi-lumen for input to said electronic interface means.

18. The control system according to claim 2, wherein each said TAP sensor is positioned externally on a body between an associated muscle, tendon, or ligament and said prosthetic or orthotic device for sensing the volitional movement of said associated muscle, tendon, or ligament.

19. A biomimetic controller comprising a plurality of pneumatic sensors, each of said for externally positioning on a body part for sensing a volitional movement of an associated muscle or tendon to cause a desired movement of another body part and generating a corresponding signal indicative of the sensed movement; and electronic interface means responsive to each said corresponding signal for analyzing said corresponding signal to provide a pattern of control signals to an output device indicative of the desired movement of said another body part.

20. The biomimetic controller according to claim 19, wherein said electronic interface means comprises:

input channel means for receiving each of said corresponding signals from said plurality of sensors;

transducer means for generating electrical signals based on said sensor signals;

signal processing means for performing digital filtering, amplification and spectral analysis for determining said pattern of control signals for output;

output means responsive to said signal processing means for providing said pattern of control signals to said output device.

21. The biomimetic controller according to claim 20, further comprising:

a microcontroller operative to control said signal processing and said output to the output device according to a particular mode of said controller; and memory means for storing information associated with said electrical signals and said mode of operation.

22. The biomimetic controller according to claim 19, wherein said plurality of sensors comprise tendon activated pneumatic (TAP) sensors.

23. The biomimetic controller according to claim 19, wherein said corresponding signal indicative of the sensed movement of said associated muscle or tendon is a pressure signal.

24. The biomimetic controller according to claim 19, wherein said another body part includes at least one finger of a hand.

25. The biomimetic controller according to claim 19, wherein said another body part includes a plurality of fingers on a hand.

26. The biomimetic controller according to claim 22, wherein said plurality of TAP sensors comprises a first TAP sensor for positioning at a first location on an arm member including a finger for sensing tendon movement associated with desired movement of said finger.

27. The biomimetic controller according to claim 26, wherein said plurality of TAP sensors further comprises a second TAP sensor positioned at a second location on said arm member for sensing tendon movement associated with desired movement of another finger.

28. The biomimetic controller according to claim 27, wherein said plurality of TAP sensors further comprises a third TAP sensor positioned at a third location on said arm member for sensing tendon movement associated with the desired movement of a third finger.

29. The biomimetic controller according to claim 28, wherein said plurality of TAP sensors further comprises a fourth TAP sensor positioned at a fourth location on said arm member for sensing tendon movement associated with desired movement of a forearm or hand.

30. The controller according to claim 26, wherein said first TAP sensor is disposed on said arm member for sensing movement associated with the extensor pollicis brevis tendon.

31. The controller according to claim 27, wherein said second TAP sensor is disposed on said arm member for sensing movement associated with the flexor digitorum superficialis tendon.

32. The controller according to claim 28, wherein said third TAP sensor is disposed on said arm member for sensing movement associated with the flexor carpi ulnaris tendon.

33. The controller according to claim 29, wherein said fourth TAP sensor is located between the ulna and radius for detecting said forearm or hand rotation.

34. The controller according to claim 19, wherein said plurality of sensors are externally positioned relative to said corresponding muscle, tendon, or ligament at predetermined locations by means of a prosthetic socket.

35. The controller according to claim 19, wherein said plurality of sensors are externally positioned relative to said corresponding muscle, tendon or ligament by means of an adjustable band circumferentially disposed around an outer surface an arm member.

36. A control system for use with a prosthetic or orthotic device comprising:

at least one pneumatic sensor for sensing volitional movement of a muscle, tendon or ligament intended to cause an associated desired movement of another body part and generating at least one signal in response thereto; and an electronic interface comprising:

an input channel for receiving said at least one signal;

a transducer for transducing said at least one signal into a corresponding at least one electronic signal to be processed;

signal processing for performing signal analysis and signal processing of said at least one electronic signal for detecting and determining the degree of movement desired of the another body part for generating said at least one control signal;

memory for storing information associated with said electronic signal; and a microprocessor for controlling the storage of said information in memory and the sending of said at least one control signal to said prosthetic or orthotic device.

* * * * *